(12) United States Patent
Makino

(10) Patent No.: US 7,962,308 B2
(45) Date of Patent: Jun. 14, 2011

(54) BODY MOTION DETECTION DEVICE, BODY MOTION DETECTION METHOD, AND BODY MOTION DETECTION PROGRAM

(75) Inventor: Kenichi Makino, Kanagawa (JP)

(73) Assignee: Sony Corporation, Tokyo (JP)

( * ) Notice: Subject to any disclaimer, the term of this patent is extended or adjusted under 35 U.S.C. 154(b) by 310 days.

(21) Appl. No.: 11/911,814

(22) PCT Filed: Feb. 20, 2007

(86) PCT No.: PCT/JP2007/053079
§ 371 (c)(1),
(2), (4) Date: Jan. 11, 2008

(87) PCT Pub. No.: WO2007/097324
PCT Pub. Date: Aug. 30, 2007

(65) Prior Publication Data
US 2008/0190201 A1 Aug. 14, 2008

(30) Foreign Application Priority Data

Feb. 22, 2006 (JP) ................. 2006-044716

(51) Int. Cl.
*G01P 15/00* (2006.01)
*G06F 17/40* (2006.01)
(52) U.S. Cl. ........ 702/141; 702/150; 702/151; 702/160; 377/24.2; 73/488
(58) Field of Classification Search .................. 702/141, 702/150, 151, 152, 160
See application file for complete search history.

(56) References Cited

U.S. PATENT DOCUMENTS

| 6,590,536 | B1* | 7/2003 | Walton ........................... 342/463 |
| 7,054,763 | B2* | 5/2006 | Kawai et al. .................... 702/42 |
| 7,450,002 | B2* | 11/2008 | Choi et al. ............... 340/539.11 |
| 2002/0103610 | A1* | 8/2002 | Bachmann et al. ............. 702/94 |
| 2006/0149420 | A1* | 7/2006 | Ikeuchi ......................... 700/245 |
| 2007/0015611 | A1* | 1/2007 | Noble et al. .................. 473/450 |
| 2009/0076765 | A1* | 3/2009 | Kulach et al. ................. 702/141 |

FOREIGN PATENT DOCUMENTS

| JP | 11-042220 | 2/1999 |
| JP | 2001-250123 | 9/2001 |
| JP | 2004-141669 | 5/2004 |
| JP | 2004-264060 | 9/2004 |
| JP | 2005-114537 | 4/2005 |
| JP | 2005-140533 | 6/2005 |
| JP | 2006-293861 | 10/2006 |

OTHER PUBLICATIONS

Translation of JP 11-042220, Feb. 16, 1999.*
Translation of JP 2001-250123, Sep. 14, 2001.*
Translation of JP 2006-293861, Oct. 26, 2006.*
U.S. Appl. No. 12/279,557, filed Aug. 15, 2008, Makino, et al.

* cited by examiner

*Primary Examiner* — Hal D Wachsman
(74) *Attorney, Agent, or Firm* — Oblon, Spivak, McClelland, Maier & Neustadt, L.L.P.

(57) ABSTRACT

A body motion detecting method calculates an acceleration-of-gravity vector from acceleration vectors, which are detection outputs of a multi-axial acceleration sensor. The method extracts a vertical component of acceleration, using the acceleration vectors from the acceleration sensor and the calculated acceleration-of-gravity vector. The method further detects peaks in the extracted vertical component of acceleration, and detects body motion in the vertical direction by analyzing the detected peaks. Related body motion detecting device and computer readable medium are also described.

22 Claims, 8 Drawing Sheets

FIG. 3

$$gx = \frac{1}{M} \sum_{n=n1-M+1}^{n1} axn \qquad \cdots (1)$$

$$gy = \frac{1}{M} \sum_{n=n1-M+1}^{n1} ayn \qquad \cdots (2)$$

$$gz = \frac{1}{M} \sum_{n=n1-M+1}^{n1} azn \qquad \cdots (3)$$

FIG. 6

$$a_n = \begin{pmatrix} a_{xn} \\ a_{yn} \\ a_{zn} \end{pmatrix} \quad \cdots (1\text{-}1)$$

$$g = \begin{pmatrix} g_x \\ g_y \\ g_z \end{pmatrix} \quad \cdots (1\text{-}2)$$

$$v_n = \frac{g^T a_n}{|g|} \quad \cdots (1\text{-}3)$$

FIG. 7

$$\theta = \tan^{-1} \frac{g_y}{g_x} \quad \cdots (2\text{-}1)$$

$$\phi = \tan^{-1} \frac{g_z}{\sqrt{(g_x)^2 + (g_y)^2}} \quad \cdots (2\text{-}2)$$

$$\begin{pmatrix} a'_{xn} \\ a'_{yn} \\ a'_{zn} \end{pmatrix} = \begin{pmatrix} \cos\phi & 0 & \sin\phi \\ 0 & 1 & 0 \\ -\sin\phi & 0 & \cos\phi \end{pmatrix} \begin{pmatrix} \cos\theta & \sin\theta & 0 \\ -\sin\theta & \cos\theta & 0 \\ 0 & 0 & 1 \end{pmatrix} a_n \quad \cdots (2\text{-}3)$$

FIG. 8

$$h_n = \sqrt{(a'_{yn})^2 + (a'_{zn})^2} \quad \cdots (3\text{-}1)$$

$$h_n = \sqrt{(a_{xn})^2 + (a_{yn})^2 + (a_{zn})^2 - (v_n)^2} \quad \cdots (3\text{-}2)$$

FIG. 9

$$a_n = \begin{pmatrix} a_{xn} \\ a_{yn} \end{pmatrix} \quad \cdots (4\text{-}1) \qquad g = \begin{pmatrix} g_x \\ g_y \end{pmatrix} \quad \cdots (4\text{-}2)$$

$$\theta = \tan^{-1} \frac{g_y}{g_x} \quad \cdots (4\text{-}3)$$

$$\begin{pmatrix} a'_{xn} \\ a'_{yn} \end{pmatrix} = \begin{pmatrix} \cos\theta & \sin\theta \\ -\sin\theta & \cos\theta \end{pmatrix} a_n \quad \cdots (4\text{-}4)$$

BODY MOTION DETECTION DEVICE, BODY MOTION DETECTION METHOD, AND BODY MOTION DETECTION PROGRAM

CROSS-REFERENCE TO RELATED APPLICATIONS

This application claims the benefit under 35 U.S.C.§119 from International Application No. PCT/JP07/53079, filed on Feb. 20, 2007, the entire contents of which is incorporated herein by reference. PCT/JP07/53079 claims the benefit of priority from Japanese Patent Application No. 2006-044716, filed on Feb. 22, 2006.

TECHNICAL FIELD

The present invention relates to a so-called body motion detecting device which detects body motion of a user (user) so as to be measured, such as a pedometer for example.

BACKGROUND ART

While many conventional pedometers have been restricted regarding the position or direction in which the main unit is worn, there have been proposed in recent years body motion detecting devices wherein the wearing position and wearing direction can be freely set. Of these, there has been proposed a method and device for using multi-axial sensors to estimate orientation, while detecting body motion using the same sensors. This is advantageous in that lower costs can be realized as compared with a method wherein angular sensors or the like are used for estimating orientation.

For example, Japanese Unexamined Patent Application Publication No. 2004-141669 discloses a method wherein acceleration is detected by multiple body motion sensors having mutually different detection directions, an operating axis is determined/selected by analyzing signal patterns from the sensors, and ambulation is detected by signal analysis of the operating axis. Also, Japanese Unexamined Patent Application Publication No. 2005-140533 discloses a method wherein mutually-orthogonal bi-axial or tri-axial acceleration sensors are implemented, wherein the direction of motion of the body motion is estimated from a resultant vector from the sensor signals from each axis, and body motion is detected by analyzing the signal components on the direction of motion which has been estimated.

DISCLOSURE OF INVENTION

Problems to be Solved by the Invention

However, the method disclosed in Japanese Unexamined Patent Application Publication No. 2004-141669 involves selecting as an operating axis only one of the multiple sensors as a sensor suitable for measurement, so there are many cases wherein the direction of body motion of the user (motion direction) to be detected and the selected operating axis do not agree, and accordingly this method is thought to be insufficient as a method for signal detection in dependent on the wearing direction of the device main unit.

Also, with the method disclosed in Japanese Unexamined Patent Application Publication No. 2005-140533, in the event that the device is hung by a hanging cord for example, noise component unrelated to the direction of movement of the user, such as pendulum moment of the device, is included in the resultant vector calculated from the sensor signals from each of the axes, and accordingly estimation of direction cannot be correctly performed. Accordingly, the method disclosed in Japanese Unexamined Patent Application Publication No. 2005-140533 is also thought to be insufficient as a method for signal detection in dependent on the wearing direction of the device main unit.

In light of the above, it is an object of the present invention to enable detection of body motion of the user in a precise manner, in accordance with the direction of body motion of the user (motion direction), without being affected by the position or direction of wearing the main unit of the device.

Means for Solving the Problems

In order to solve the above problems, a body motion detecting device according to an embodiment of the invention comprises:
a multi-axial acceleration sensor;
acceleration-of-gravity calculating means for calculating an acceleration-of-gravity vector from acceleration vectors, which are detection output of the multi-axial acceleration sensor;
vertical component extracting means for extracting a vertical component of acceleration, using the acceleration vector from the acceleration sensor and the acceleration-of-gravity vector calculated by the acceleration-of-gravity calculating means; and
vertical body motion detecting means for detecting body motion in the vertical direction by analyzing the vertical component of acceleration, extracted by the vertical component extracting means.

According to an embodiment of the body motion detecting device, acceleration-of-gravity calculating means perform computation processing on acceleration vectors, which are detection output of a multi-axial acceleration sensor, thereby calculating an acceleration-of-gravity vector. The calculated acceleration-of-gravity vector is supplied to vertical component extracting means, where predetermined computation processing is performed taking into consideration the acceleration vector as well, thereby extracting the vertical component included in the acceleration vector. This vertical component is analyzed by vertical body motion detecting means, whereby vertical direction body motion of the user can be accurately detected.

Thus, an acceleration-of-gravity vector is obtained from acceleration vectors which are detection output of an acceleration sensor, and the acceleration-of-gravity vector and acceleration vector are comprehensively used to obtain the vertical component of the acceleration vector, whereby the vertical direction body motion of the user can be accurately detected without being affected by the wearing position and wearing direction of the body motion detecting device.

Also, a body motion detecting device according to an embodiment of the invention comprises:
a multi-axial acceleration sensor;
acceleration-of-gravity calculating means for calculating an acceleration-of-gravity vector from acceleration vectors, which are detection output of the multi-axial acceleration sensor;
horizontal component extracting means for extracting a horizontal component of acceleration, based on a computational expression corresponding to an angle of deviation in three-dimensional space of the acceleration vector from the acceleration sensor and the acceleration-of-gravity vector calculated by the acceleration-of-gravity calculating means; and horizontal body motion detecting means for detecting body motion in the horizontal direction by analyzing the horizontal component of acceleration, extracted by the horizontal component extracting means.

According to the body motion detecting device of an embodiment, acceleration-of-gravity calculating means perform computation processing on acceleration vectors, which are detection output of a multi-axial acceleration sensor, thereby calculating an acceleration-of-gravity vector. The calculated acceleration-of-gravity vector is supplied to horizontal component extracting means, where the horizontal component included in the acceleration vector is extracted based on a predetermined computation expression taking into consideration the acceleration vector, and the deviation angle of the acceleration-of-gravity vector in three-dimensional space. This horizontal component is analyzed by horizontal body motion detecting means, whereby horizontal direction body motion of the user can be accurately detected.

Thus, an acceleration-of-gravity vector is obtained from acceleration vectors which are detection output of an acceleration sensor, and the acceleration vector and acceleration-of-gravity vector are comprehensively used to obtain the horizontal component of the acceleration vector, whereby the horizontal direction body motion of the user can be accurately detected without being affected by the wearing position and wearing direction of the body motion detecting device.

Advantages

Stable body motion detection can be realized, by preventing difference in detection precision of the body motion of the user from occurring under effects of the wearing position and wearing direction of the user as to the device. Also, this can be realized without necessitating additional sensor such as angle sensors or the like.

BRIEF DESCRIPTION OF THE DRAWINGS

FIG. 3 is a diagram for describing calculation expressions for acceleration-of-gravity vector in the pedometer shown in FIG. 1.

FIG. 6 is a diagram for describing an acceleration vector an, an acceleration-of-gravity vector g, and a vertical component vn of the acceleration vector an, in a case of using a tri-axial acceleration sensor.

FIG. 7 is a diagram for describing a case of calculating the vertical component vn of the acceleration vector an, taking into consideration the deviation angle of the acceleration-of-gravity vector g, in a case of using a tri-axial acceleration sensor.

FIG. 8 is a diagram for describing a case of calculating a vertical component hn of the acceleration vector an, in a case of using a tri-axial acceleration sensor.

FIG. 9 is a diagram for describing the acceleration vector an, the acceleration-of-gravity vector g, and the vertical component vn of the acceleration vector an, in a case of using a bi-axial acceleration sensor.

BEST MODE FOR CARRYING OUT THE INVENTION

Figure 1:
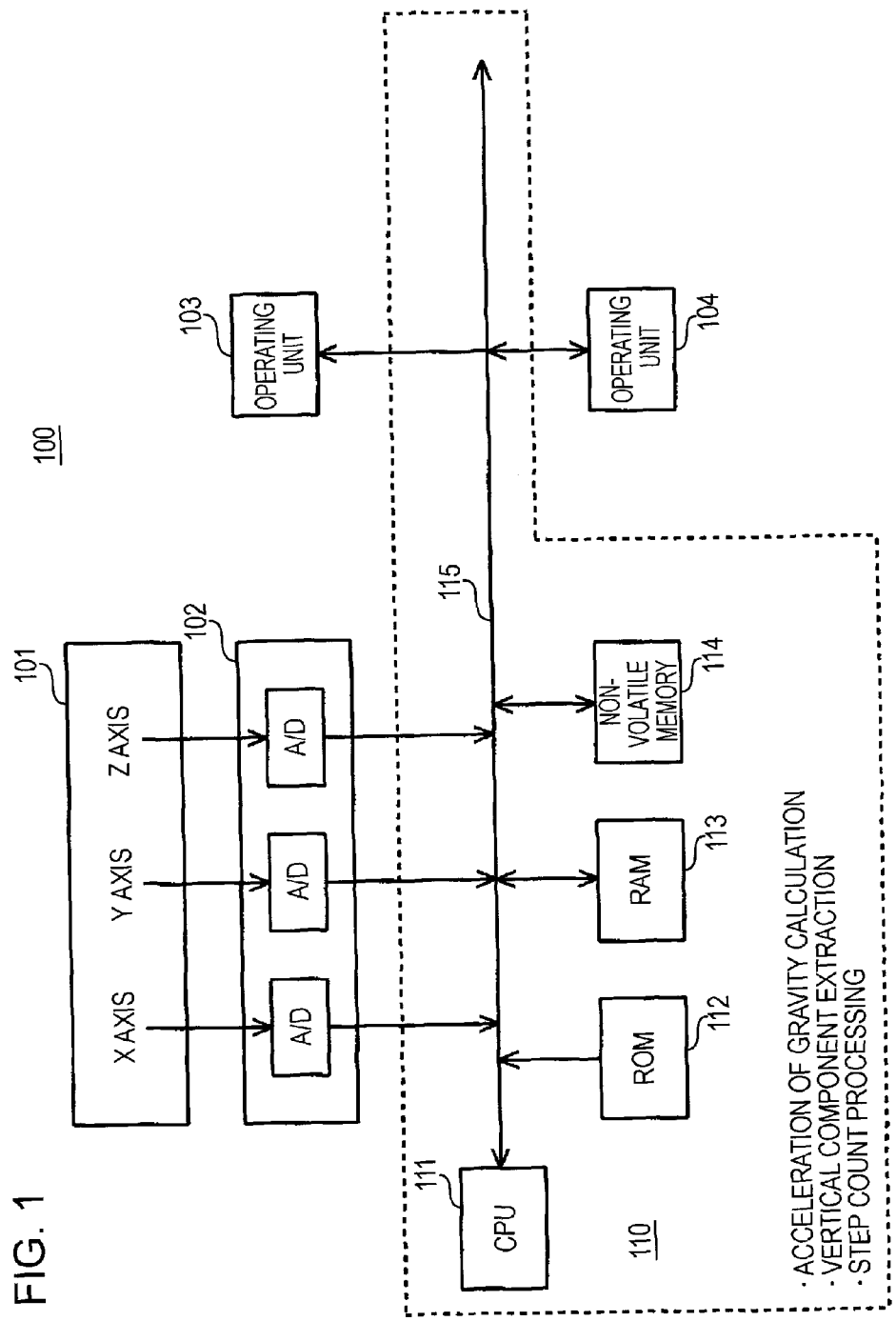
FIG. 1 is a block diagram for describing a pedometer to which a first embodiment of the present invention has been applied.

An embodiment of the device, method, and program according to the present invention will be described with reference to the drawings.

Basic Idea of the Present Invention

First, prior to specific description of an embodiment of the device, method, and program according to the present invention, the basic idea of the present invention will be described to facilitate describing of this embodiment. To put the basic idea of the present invention simply, it is to "(1) use a multi-axial acceleration sensor configured of mutually-orthogonal axes, and estimate an acceleration-of-gravity vector in that gravitational field using the detection output from the multi-axial acceleration sensor, and (2) extract vertical direction signal components from the detection output from the same acceleration sensor, based on estimation results of the acceleration-of-gravity vector."

Extracting the vertical component by comprehensively using detection output from all axes of the multi-axial acceleration sensor in this way enables precise detection of at least the vertical direction motion of the user without being affected by the wearing position and wearing direction of the user as to the acceleration sensor, with no need to estimation of an operating axis.

Now, a case of using a tri-axial acceleration sensor will be described in detail. We will say that the acceleration sensor has the three axes of X axis, Y axis, and Z axis, with the acceleration vector an at a certain point-in-time, obtained from the acceleration sensor, as $a_{xn}$ (X-axial component), $a_{yn}$ (Y-axial component), and $a_{zn}$ (Z-axial component), as shown in Expression (1-1) in FIG. 6. The acceleration-of-gravity vector g is estimated from the acceleration vector (data series of acceleration vector) shown in Expression (1-1) in FIG. 6, and body motion detection is also performed.

Specifically, estimation of the acceleration-of-gravity vector g can be performed more simply by a method of calculating the average movement value of each axis of the acceleration vector an, and taking the average vector thereof as the acceleration-of-gravity vector g. In this case, movement average should be calculated over a sufficiently long period, in order to reduce effects of body motion on the signal components. Also, a method can be used such as analyzing the values of each axis of the acceleration vector an using least square to calculate the acceleration-of-gravity vector g.

The results of estimation of the acceleration-of-gravity vector g using the acceleration vector an are to be expressed by $g_x$ (X-axial component), $g_y$ (Y-axial component), and $g_z$ (Z-axial component), as shown in Expression (1-2) in FIG. 6. In this case, the vertical component vn of the acceleration vector an can be obtained by the computation shown in shown in Expression (1-3) in FIG. 6. That is to say, the vertical component vn of the acceleration vector an can be obtained by dividing the product of the inner product of the acceleration-of-gravity vector g and the acceleration vector an, by the absolute value (magnitude) of the acceleration-of-gravity vector g, as shown in Expression (1-3) in FIG. 6.

Thus, the vertical component vn can be precisely obtained by computation from the acceleration vector an detected by the tri-axial acceleration sensor, and the acceleration-of-gravity vector g obtained from this acceleration vector. That is to say, the present invention is based upon the idea that the vertical direction body motion of the user can be precisely detected, by comprehensively using detection output from a multi-axial acceleration sensor and separating only the vertical component therefrom by numerical calculation.

Also, a similar calculation can be preformed by first obtaining the deviation angle of the acceleration-of-gravity vector g in three-dimensional space and then rotating the acceleration vector an. That is, expressing the deviating angles θ and φ as shown in (2-1) and (2-2) in FIG. 7, the a'xn calculated by Expression (2-3) in FIG. 7 is the vertical component of the acceleration vector an, and a'xn agrees with the vertical component vn. Also, the inner product of the vector a'yn and vector a'zn is the orthogonal projection of the acceleration vector an onto a plane of which the acceleration-of-gravity vector g is the normal vector.

That is to say, the acceleration vector an obtained from the detection output from the tri-axial acceleration sensor can be divided into the components of the vertical component and horizontal components, so in addition to the vertical component, horizontal direction body motion can be detected by analyzing the horizontal components. Specifically, the length hn of the horizontal vector can be obtained by Expression (3-1) in FIG. 8 and Expression (3-2) in FIG. 8.

Thus, in the way of using a computation expression taking into consideration the deviation angles of the acceleration-of-gravity vector, the vertical direction body motion and horizontal direction body motion of the user can be obtained relatively easily, and furthermore precisely.

Note that while an example has been described here regarding a case of using a tri-axial acceleration sensor, the present invention is not restricted to this. The basic concept of the present invention can be applied to a case of using a bi-axial acceleration sensor in the same manner as with the case of using a tri-axial acceleration sensor.

That is to say, expressing the acceleration vector an from a bi-axial acceleration sensor and the acceleration-of-gravity vector g as shown in Expression (4-1) in FIG. 9 (acceleration vector) and Expression (4-2) in FIG. 9 (acceleration-of-gravity vector), the vertical component can be calculated following Expression (1-3) in FIG. 6, in the same way as with using a tri-axial acceleration sensor. Expressing the deviation angle θ of the acceleration-of-gravity vector g as shown in Expression (4-3) in FIG. 9, the acceleration vector an can be divided into the vertical component a'xn and the horizontal component a'yn orthogonal thereto following Expression (4-4) in FIG. 9, and a'xn and the vertical component vn agree.

In this way, the vertical direction body motion of the user can be precisely detected by the Expression shown in FIG. 9 and Expression (1-3) in FIG. 6 even in the case of using a bi-axial acceleration sensor, and in the event of taking into consideration the deviation angle θ of the acceleration-of-gravity vector g, the horizontal direction body motion of the user can also be precisely detected.

FIG. 10A through FIG. 10D illustrate in the form of graphs showing acceleration data acquired for four seconds at a sampling frequency of 50 Hz with a tri-axial acceleration sensor worn by a user while the user is exercising such as walking, and data obtained in a case of performing component breakdown following the above-described basic concept of the present invention.

Figure 10A:
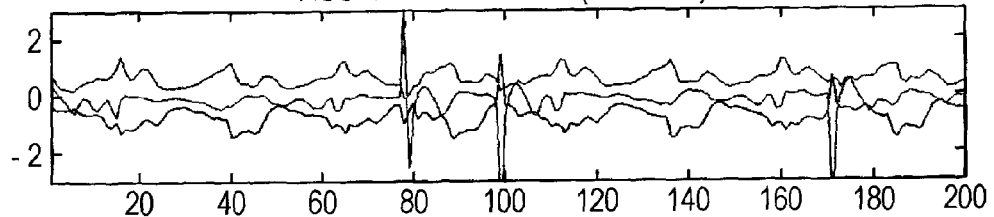
FIG. 10A is a diagram for describing an example of an acceleration data graph.
Figure 10B:
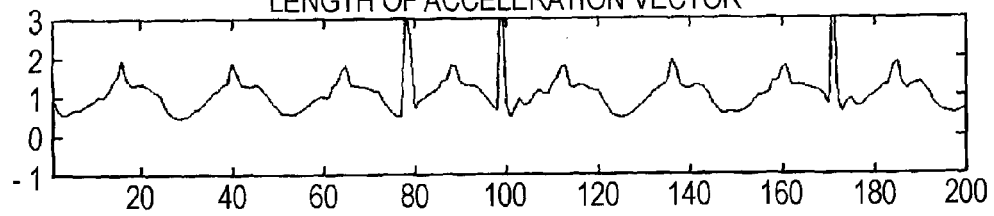
FIG. 10B is a diagram for describing an example of the length of an acceleration vector.
Figure 10C:
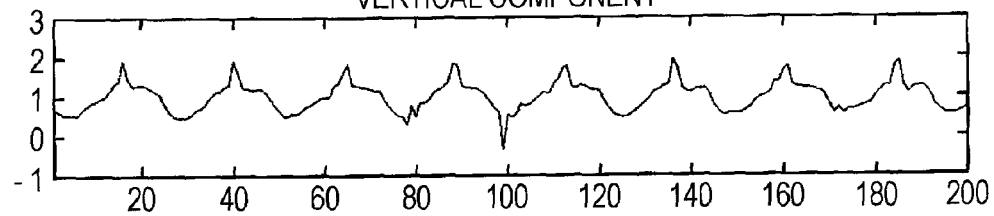
FIG. 10C is a diagram for describing an example of vertical component.
Figure 10D:
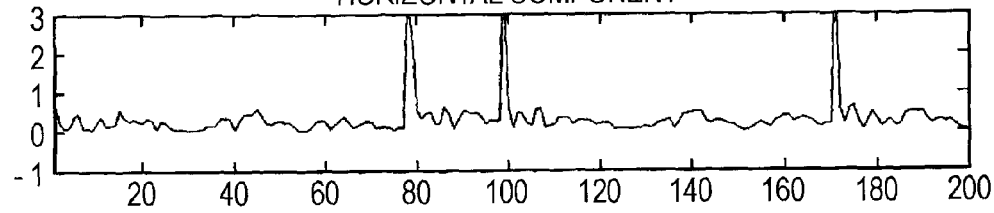
FIG. 10D is a diagram for describing an example of horizontal component.

That is to say, FIG. 10A is a graph of acceleration data from the tri-axial acceleration sensor, FIG. 10B is a graph of the length (magnitude) of the acceleration vector calculated from the tri-axial acceleration data, and FIG. 10C is a graph of the vertical component obtained by calculation from the tri-axial acceleration data with the method described using FIG. 6 through FIG. 8. Also, FIG. 10D is a graph of horizontal component obtained by calculation from the tri-axial acceleration data with the method described using FIG. 6 through FIG. 8.

The graphs shown in FIG. 10A through FIG. 10D illustrate a case wherein, at the time of detecting acceleration data, the user was performing primarily vertical direction motion, but horizontal direction motion occurs at around the 80th sample, around the 100th sample, and around the 170th sample, which exist as a noise component.

However, the noise component exists in the horizontal component, so in accordance with the basic concept of the present invention, the horizontal component noise can be removed form the vertical component by component breakdown of the acceleration data (acceleration vector) into vertical component (FIG. 10C) and horizontal component (FIG. 10D), so it can be understood that the vertical direction body motion of the user can be accurately detected. Of course, vertical component noise can be removed form the horizontal component, so horizontal direction body motion of the user can be accurately detected. That is to say, component breakdown has the advantage of reduced noise.

Specific Application Example of the Invention

An embodiment of the device, method, and program according to the present invention, realized by applying the basic idea of the invention as described above, will now be described in detail.

[Application to a Pedometer]

First, an example of applying the device, method, and program according to the present invention, to a pedometer, will be described. FIG. 1 is a block diagram for describing a pedometer 100 according to the present embodiment. As shown in FIG. 1, the pedometer 100 according to the present embodiment is configured with a tri-axial acceleration sensor 101 being connected to a control unit 110 via an A/D converter 102, and also a display unit 103 and operating unit 104 being connected.

The tri-axial acceleration sensor 101 may be either an arrangement wherein uni-axial acceleration sensors are arrayed on the three mutually orthogonal X axis, Y axis, and Z axis, or may be an arrangement wherein acceleration sensors of the three mutually orthogonal axes are sealed into a package. The detection output (analog output) from each of the X axis, Y axis, and Z axis of the tri-axial acceleration sensor 101 is supplied to the A/D converter 102, converted here into digital data which can be processed at the control unit 110, and supplied to the control unit 110.

The control unit 110 is for controlling the components of the pedometer 100 according to the present embodiment, and as shown in FIG. 1, is configured of a CPU (Central Processing Unit) 111, ROM (Read Only Memory) 112, RAM (Random Access Memory) 113, and non-volatile memory 114 being connected via a CPU bus 115 so as to assume the configuration of a microcomputer.

Now, the CPU 111 is the main entity for processing and controlling at the control unit 110, such as executing various types of programs, forming control signals to be supplied to the components, performing various types of computation, and so forth. The ROM 112 stores and holds various types of programs and data necessary for processing.

Also, the RAM 113 is used primarily as a work area, such as temporarily storing partway results of processing, and so forth. The non-volatile memory 114 is memory such as EEPROM (Electrically Erasable and Programmable ROM) or flash memory for example, wherein stored data is not erased even if the power is turned off, and stores and holds data which should be held even if the power is turned off, such as set parameters, added programs, and so forth.

The display unit 103 connected to the control unit 110 includes a display control circuit, has a display device such as, for example, an LCD (Liquid Crystal Display), organic EL (Electro Luminescence) display, CRT (Cathode-Ray Tube) or the like, and displays the count value of step, various types of guidance information, and so forth, in accordance with control by the control unit 110. Specifically, the display 103 receives supply of display data from the control unit 110, forms picture signals to be supplied to the display device based on the display data, and supplies this to the display device, thereby displaying the display information corresponding to the display data form the control unit 110 on the display screen of the display device.

Also, the operating unit 104 has a reset key, various types of function keys, and so forth, and can accept operation input from the user and supply electrical signals corresponding thereto to the control unit 110. The control unit 110 controls the components accordingly, such that processing according to instructions from the user an be performed.

With the pedometer 100 according to the present embodiment, the control unit 110 is supplied with detection output from the tri-axial acceleration sensor 101 (acceleration vector data), and calculates the acceleration-of-gravity vector from the detection output, based on predetermined calculation expressions. The control unit 110 extracts the vertical component of the acceleration vector, based on predetermined calculation expressions taking into consideration the acceleration-of-gravity vector that has been calculated and the acceleration vector from the tri-axial acceleration sensor 101.

The control unit 110 then detects the body motion of the user in the vertical direction, i.e., the body motion corresponding to walking, by analyzing the extracted vertical component of the acceleration vector, and counts these, whereby the number of steps of the user can be accurately measured. That is to say, the control unit 110 realizes functionality as acceleration-of-gravity calculating means, functionality as vertical component extracting means, functionality as vertical body motion detecting means for detecting vertical direction body motion, and functionality as counting means for counting the detected vertical direction body motions.

Figure 2:
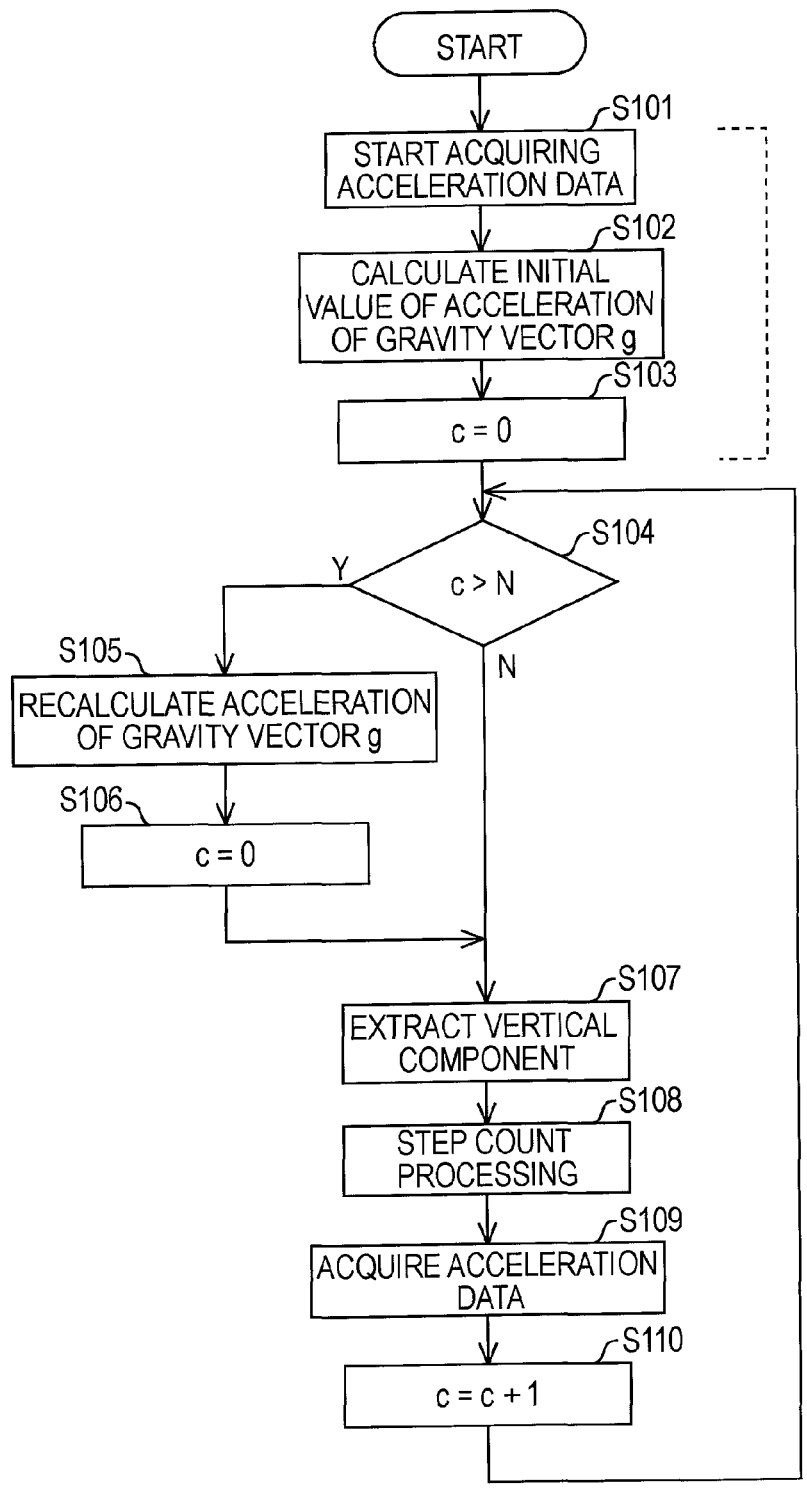
FIG. 2 is a flowchart for describing processing which is executed in the pedometer shown in FIG. 1.

FIG. 2 is a flowchart for describing processing for performing step counting, which is executed primarily in the control unit 110 of the pedometer 100 according to the embodiment shown in FIG. 1. Upon the power being turned on to the pedometer 100 according to the present embodiment, and receiving instruction input for executing measuring of steps via the operating unit 104, the CPU 111 of the control unit 110 executes the processing shown in FIG. 2.

First, the control unit 110 starts acquiring acceleration data (acceleration vectors) supplied via the A/D converter 102 (step S101), an calculates the initial value of the acceleration-of-gravity vector g (step S102). The sample counter c is then rest (zero-cleared) (step S103). The processing from step S101 through step S103 is equivalent to the so-called initial processing after turning the power on.

The control unit 110 then determines whether or not the sample counter c value is greater than a predetermined value N (step S104). With this embodiment, recalculation of the acceleration-of-gravity vector g is performed every N (N is an integer of 1 or greater) samples, in order to reduce the amount of calculation.

In the event that determination is made in the determining processing in step S104 that the sample counter c value is greater than the stipulated value N, the control unit 110 performs recalculation processing of the acceleration-of-gravity vector g (step S105), and subsequently sets the sample counter c to the value 0 (step S106). That is to say, the processing of step S106 is resetting processing of the sample counter c.

In the event that determination is made in the determining processing in step S104 that the sample counter c value is not greater than the stipulated value N, the control unit 110 extracts the vertical component vn of the acceleration vector using the initial value of the acceleration-of-gravity vector g calculated in step S102 and the acceleration vector an (step S107).

That is to say, in the present embodiment, the recalculation processing of the acceleration-of-gravity vector g in step S105 and calculation processing of the initial value of the acceleration-of-gravity vector in step S102 are basically the same processing, with the acceleration-of-gravity vector g being calculated by taking the movement average of the data of each axis of the acceleration value as an estimation value of acceleration of gravity.

To describe in detail the processing performed in step S103 and step S105, in a case of obtaining the acceleration of gravity from M samples worth of past acceleration data, with the current sample position at n1, the calculations shown in FIG. 3 can be used. That is to say, in the event of obtaining the acceleration-of-gravity vector gx of the X axis, the acceleration data axn of the X axis for each sample from a position M+1 samples earlier than the current sample position up to n1 is added, the total value is obtained, and this total value is divided by the value M, whereby the acceleration-of-gravity vector gx for the X axis can be obtained, as shown in Expression (1) in FIG. 3.

In the same way, in the event of obtaining the acceleration-of-gravity vector gy of the Y axis, the acceleration data ayn of the Y axis for each sample from a position M+1 samples earlier than the current sample position up to n1 is added, the total value is obtained, and this total value is divided by the value M, whereby the acceleration-of-gravity vector gy for the Y axis can be obtained, as shown in Expression (2) in FIG. 3. Also, in the event of obtaining the acceleration-of-gravity vector gz of the Z axis, the acceleration data azn of the Z axis for each sample from a position M+1 samples earlier than the current sample position up to n1 is added, the total value is obtained, and this total value is divided by the value M, whereby the acceleration-of-gravity vector gz for the Z axis can be obtained, as shown in Expression (3) in FIG. 3.

In the event of calculating the acceleration-of-gravity vector according to the calculation expressions shown in FIG. 3, an average should be taken over a sufficiently long period such that the acceleration component due to movement is averaged and cancelled. However, this should be set to around several seconds for example, since if this is too long, the inclination of the device cannot be followed (the inclination of the device cannot be properly reflected).

In the extracting processing of the vertical component in step S107, the vertical component vn can be obtained (extracted) based on the newest acceleration vector an and the acceleration-of-gravity vector g, according to the Expression (1-3) shown in FIG. 6 or the Expression (2-3) shown in FIG.

7. The vertical component vn thus obtained exhibits peaks corresponding to the vertical motion accompanying walking motion of the user.

Accordingly, the control unit 110 can detect vertical direction body motion of the user by determining the vertical component extracted in step S107 by a threshold as suitable, and the number of steps corresponding to walking of the user can be accurately counted by counting these (step S108).

The control unit 110 then acquires the newest acceleration vector from the tri-axial acceleration sensor 101 (step S109), increments the sample counter c by 1 (step S110), and repeats the processing from step S104.

Thus, the pedometer 100 according to the present embodiment is provided with the acceleration vector an from the tri-axial acceleration sensor 101, calculates the acceleration-of-gravity vector g, and thus can extract the vertical component vn of the acceleration vector an by numeric calculation using the from the acceleration-of-gravity vector g and the acceleration vector an.

The vertical component extracted from the measurement data at the time of the user walking while wearing the pedometer 100 according to the present embodiment on his/her body exhibits peaks corresponding to the vertical motion accompanying walking, so as described above as well, walking can be counted by suitable threshold determination. That is to say, in a case of the user wearing the pedometer 100 on the body, a pedometer can be realized which can accurately measure the number of steps of the user by wearing at a suitable position on the body of the user, without being affected by the wearing position or wearing direction of the pedometer such that an operating axis can be set as intended.

Note that with the pedometer 100 according to the present embodiment, estimation of the acceleration of gravity is performed every N samples in order to reduce the amount of computations, as shown in FIG. 2, but the present is not restricted to this. Estimation of the acceleration of gravity may also be performed every sample. Computation processing for estimation of the acceleration of gravity is not restricted to obtaining the movement average of the data for each axis. For example, a method such as least square or the like may be used.

Note that the processing in the flowchart shown in FIG. 2 corresponds to the method of the present invention. In the above, the control unit 110 has been described as realizing the functionality as acceleration-of-gravity calculating means, functionality as vertical component extracting means, functionality as vertical body motion detecting means for detecting vertical direction body motion, and functionality as counting means for counting the detected vertical direction body motions.

That is to say, creating a program (software) which executes the processing of each step in the flowchart shown in FIG. 2, and storing this in the ROM 112 of the control unit 110, enables the above-described pedometer 100 to be realized. Of course, an arrangement can be made wherein the functionality as acceleration-of-gravity calculating means, functionality as vertical component extracting means, functionality as vertical body motion detecting means for detecting vertical direction body motion, and functionality as counting means for counting the detected vertical direction body motions, are each configured of different circuits.

[Application to User Interface Device]

Next, an example of applying the device, method, and program according to the present invention, to a user interface device, will be described. The user interface device 200 according to the present embodiment can detect horizontal direction body motion of a user, and control operations of a device using this as input information from the user.

Figure 4:
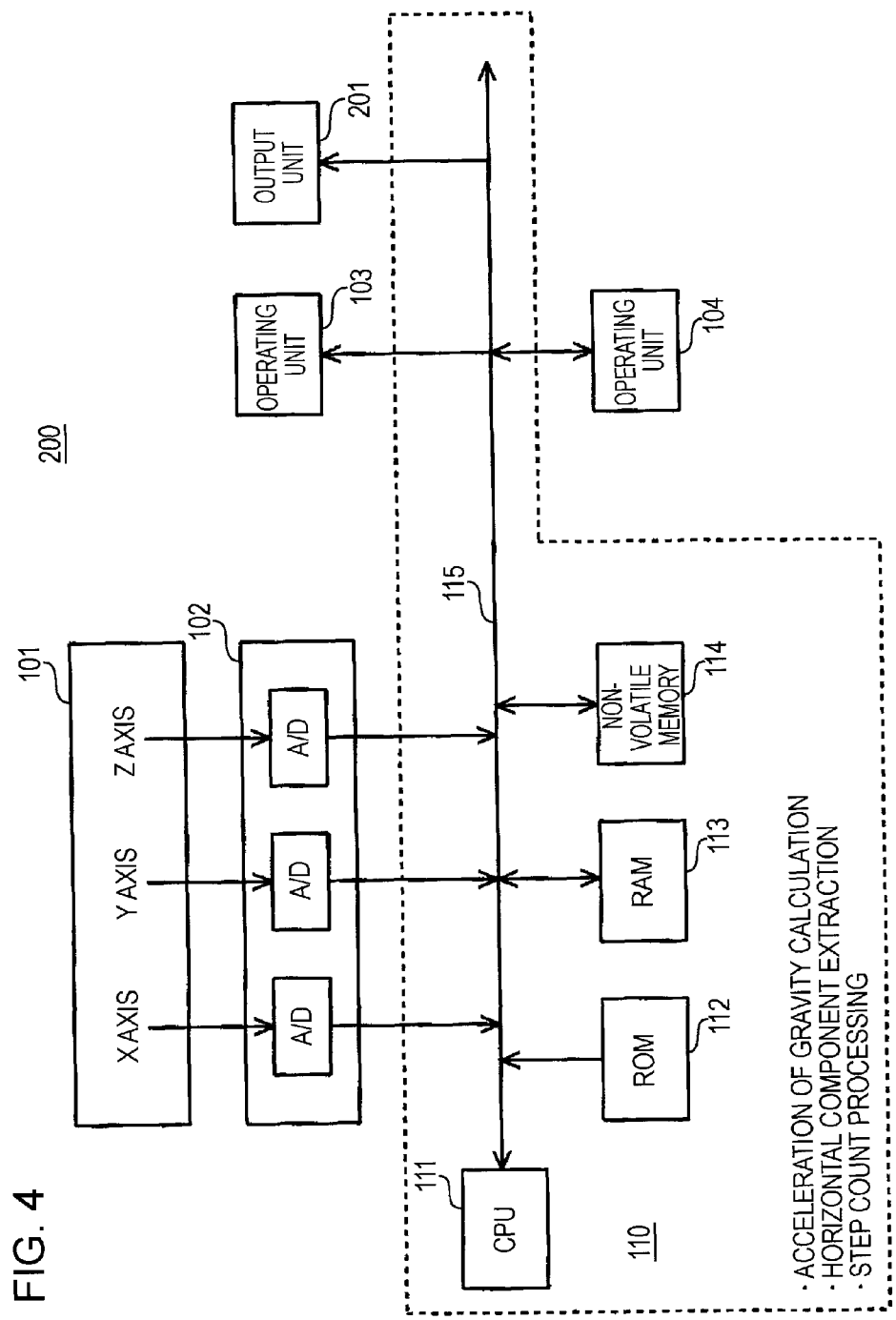
FIG. 4 is a block diagram for describing a user interface device to which an embodiment of the present invention has been applied.

FIG. 4 is a block diagram for describing the user interface device 200 according to the present embodiment. As shown in FIG. 4, the user interface device 200 is configured in the same way as with the pedometer 100 shown in FIG. 1 except for the point that an output unit 201 has been provided. Accordingly, with the user interface device 200 shown in FIG. 4, portions configured in the same way as with the pedometer 100 shown in FIG. 100 are denoted with the same reference numerals, and detailed description of such portions will be omitted.

The user interface device 200 differs in that while the pedometer 100 described with reference to FIG. 1 performed extraction/processing of the vertical component vn of the acceleration vector an from the acceleration sensor 101, the user interface device 200 performs extraction/processing of the horizontal component hn of the acceleration vector an from the acceleration sensor 101.

With the user interface device 200 according to the present embodiment, in the event of detecting body motion of the user in the horizontal direction, the output unit 201 outputs a signal for notification thereof, and supplies this to an external device, whereby the external device can be controlled. In this case, the output unit 201 is a portion which is realized as a transmission unit of an infra-red remote controller signal, formed of an infra-red light emitting unit, a transmission unit of a wireless electric wave signal, or an output terminal for transmitting electric signals to an external device connected by wires, or the like.

The user interface device 200 according to the present embodiment is used by the user holding in the hand, and in the event of detecting that the user has shaken the user interface device 200 horizontally, a power source on/off signal is generated for example, which is transmitted via the output unit 201 to the external device, so as to remotely control the external device.

AS for operations other than on/off of the power source, signals corresponding to operation input from the user which has been accepted via the operating unit 104 are generated at the control unit 110, and transmitting these to the other device via the output unit 201 enables various types of remote control to be performed. AS described above, turning the power source on/off can be performed simply by shaking the user interface device horizontally, and also, there is no on/off of the power source even if shaken vertically, so erroneous operations can also be prevented.

With this user interface device 200 as well, the control unit 110 is supplied with detection output from the tri-axial acceleration sensor 101 (acceleration vector data), and calculates the acceleration-of-gravity vector from the detection output, based on predetermined calculation expressions. The control unit 110 extracts the vertical component of the acceleration vector, based on predetermined calculation expressions taking into consideration the acceleration-of-gravity vector that has been calculated and the acceleration vector from the tri-axial acceleration sensor 101.

The control unit 110 then detects the body motion of the user in the horizontal direction, i.e., whether or not the user has shaken the user interface device 200 in the horizontal direction, by analyzing the horizontal component of the acceleration vector which has been extracted, and in the event that the user has shaken in the horizontal direction, a power source on/off control signal can be formed and transmitted from the output unit 201.

That is to say, with the user interface device 200, the control unit 110 realizes functionality as acceleration-of-gravity calculating means, functionality as horizontal component extracting means, functionality as horizontal body motion detecting means for detecting horizontal direction body motion, and functionality as control means for forming control signals corresponding to the detected horizontal direction body motions.

Figure 5:
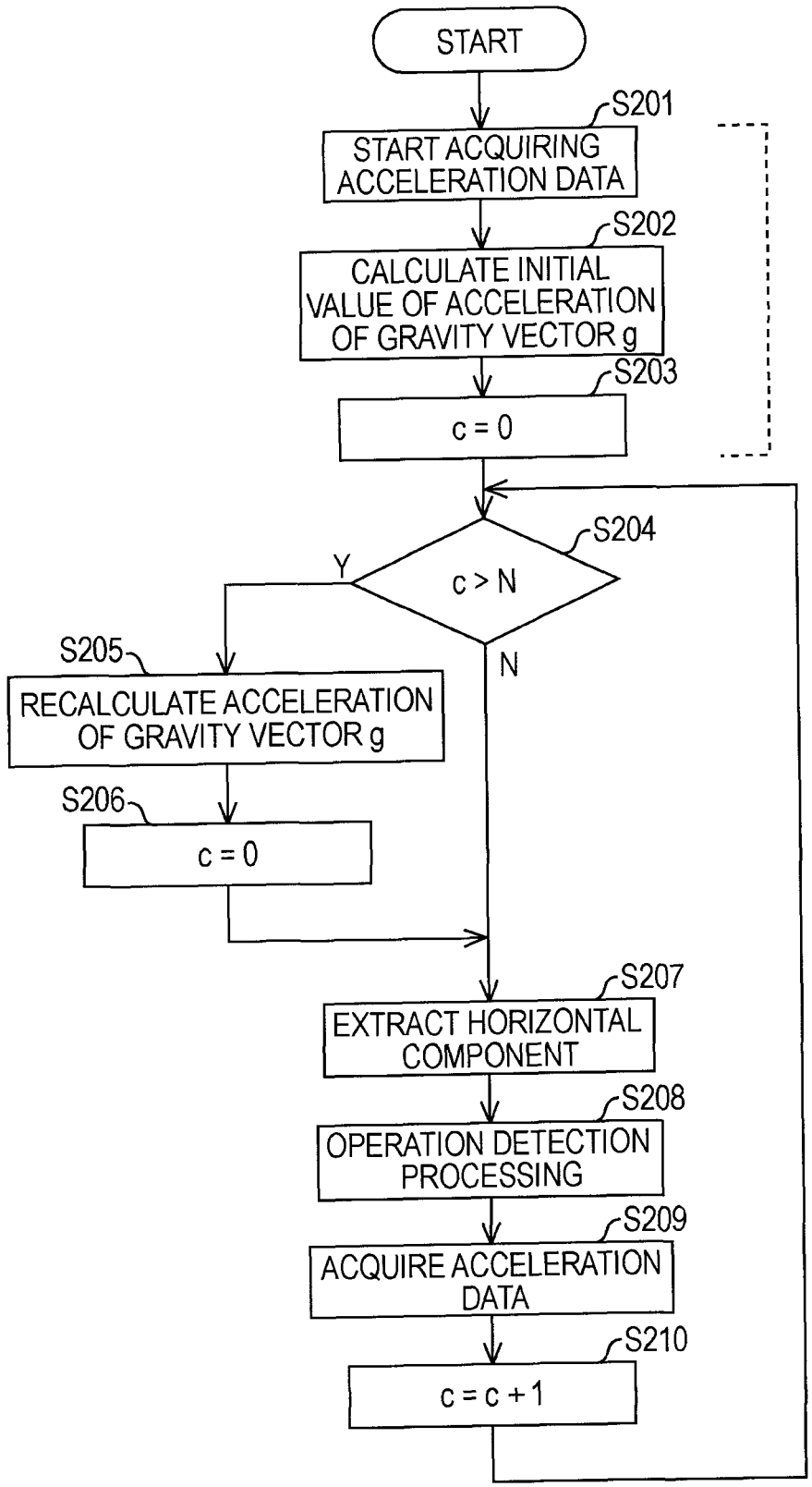
FIG. 5 is a flowchart for describing the processing executed at the user interface device shown in FIG. 4.

FIG. 5 is a flowchart for describing processing which is executed primarily in the control unit 110 of the user interface device 200 according to the embodiment shown in FIG. 4. Upon the power being turned on to the user interface device 200 according to the present embodiment, and receiving instruction input for executing measuring of steps via the operating unit, the CPU 111 of the control unit 110 executes the processing shown in FIG. 5.

First, the control unit 110 starts acquiring acceleration data (acceleration vectors) supplied via the A/D converter 102 (step S201), an calculates the initial value of the acceleration-of-gravity vector g (step S202). The sample counter c is then rest (zero-cleared) (step S203). The processing from step S201 through step S203 is equivalent to the so-called initial processing after turning the power on.

The control unit 110 then determines whether or not the sample counter c value is greater than a predetermined value N (step S204). With this user interface device 200 as well, recalculation of the acceleration-of-gravity vector g is performed every N (N is an integer of 1 or greater) samples, in order to reduce the amount of calculation, in the same way as with the processing of the pedometer 100 described with reference to FIG. 2.

In the event that determination is made in the determining processing in step S204 that the sample counter c value is greater than the stipulated value N, the control unit 110 performs recalculation processing of the acceleration-of-gravity vector g (step S205), and subsequently sets the sample counter c to the value 0 (step S206). That is to say, the processing of step S206 is resetting processing of the sample counter c.

In the event that determination is made in the determining processing in step S204 that the sample counter c value is not greater than the stipulated value N, the control unit 110 extracts the horizontal component hn of the acceleration vector using the initial value of the acceleration-of-gravity vector g calculated in step S202 and the acceleration vector an (step S207).

That is to say, with the processing shown in FIG. 5 as well, the recalculation processing of the acceleration-of-gravity vector g in step S205 and calculation processing of the initial value of the acceleration-of-gravity vector in step S202 are basically the same processing, with the acceleration-of-gravity vector g being calculated by taking the movement average of the data of each axis of the acceleration value as an estimation value of acceleration of gravity. Specific processing performed in step S203 and step S205 is as has been described with reference to FIG. 3.

In the extracting processing of the horizontal component in step S207, the horizontal component hn can be obtained (extracted) based on the newest acceleration vector an and the acceleration-of-gravity vector g, according to the Expression (2-3) shown in FIG. 7 and the Expression (3-1) shown in FIG. 8, or the Expression (3-2) shown in FIG. 8. The horizontal component vn thus obtained exhibits peaks corresponding to the motion accompanying the user shaking the user interface device horizontally.

Accordingly, the control unit 110 detects horizontal direction body motion of the user by determining the horizontal component extracted in step S207 by a threshold as suitable, and in the event of detection, forms control signals corresponding thereto and outputs these (step S208). The control unit 110 then acquires the newest acceleration vector from the tri-axial acceleration sensor 101 (step S209), increments the sample counter c by 1 (step S210), and repeats the processing from step S204.

Thus, the user interface device 200 according to the present embodiment is provided with the acceleration vector an from the tri-axial acceleration sensor 101, calculates the acceleration-of-gravity vector g, and thus can extract the horizontal component hn of the acceleration vector an by numeric calculation using the from the acceleration-of-gravity vector g and the acceleration vector an.

With the case of the user interface device 200 as well, in the same way as the above-described case of the pedometer 100, the actions of the user holding the user interface device and shaking in the horizontal direction can be accurately detected and used, without being affected by the direction of the user holding the user interface device 200 or the way in the which the user is holding the user interface device 200.

Note that with the user interface device 200 according to the present embodiment, estimation of the acceleration of gravity is performed every N samples in order to reduce the amount of computations as shown in FIG. 5, but the present is not restricted to this. Estimation of the acceleration of gravity may also be performed every sample. Computation processing for estimation of the acceleration of gravity is not restricted to obtaining the movement average of the data for each axis. For example, a method such as least square or the like may be used.

Note that the processing in the flowchart shown in FIG. 4 corresponds to the method of the present invention. In the above, the control unit 110 has been described as realizing the functionality as acceleration-of-gravity calculating means, functionality as horizontal component extracting means, functionality as horizontal body motion detecting means for detecting horizontal direction body motion, and functionality as control means for forming control signals corresponding to the detected horizontal direction body motions.

That is to say, creating a program (software) which executes the processing of each step in the flowchart shown in FIG. 2, and storing this in the ROM 112 of the control unit 110, enables the above-described user interface device 200 to be realized. Of course, an arrangement can be made wherein the functionality as acceleration-of-gravity calculating means, functionality as horizontal component extracting means, functionality as horizontal body motion detecting means for detecting horizontal direction body motion, and functionality as control means for forming control signals corresponding to the detected horizontal direction body motions, are each configured of different circuits.

Also, the user interface device 200 here has been described as forming power source on/off signals for example, and transmitting to an external device, in the event of the user shaking in the horizontal direction. Various external devices can be conceived for this, such as television receivers, radio receivers, playback devices and recording/playback devices such as VTR (Video Tape Recorder) and DVD players and CD players and so forth, and various types of other electronic devices.

Also, various types of portable electronic devices, such as portable music playback devices, cellular telephone terminals, portable information terminals, and so forth, are in use, and arrangements may be made wherein the above-described user interface device 200 is implemented in such devices, so that control is executed in a case of detecting horizontal direction body motion, such as in the event of shaking in the horizontal direction, the power source turns on if off and turns off if on, and so forth.

Of course, an arrangement may be made regarding this case wherein, in the event of turning off the power source when in an on state, determination is made regarding whether or not processing is being executed, and the power source is turned off only in cases wherein processing is not be executed, and in cases wherein some sort of processing is being executed a warning sound is emitted so as to effect control such that the power source is not turned off in situations where turning off the power source would cause trouble.

Also, while the above-described embodiment has been arranged such that vertical direction body motion is detected with the pedometer 100 and horizontal direction body motion is detected with the user interface device 200, but the invention is not restricted to this. Detection of vertical direction body motion and detection of horizontal direction body motion may be performed with a single device.

For example, with the pedometer 100, an arrangement wherein horizontal direction body motion is detected would allow for turning the power source on/off by shaking the pedometer 100 in the horizontal direction, and following turning on the power source, functions as a pedometer which accurately measures steps by detecting and counting vertical direction body motions.

Also, with the user interface device 200, an arrangement wherein vertical direction body motion is detected would allow for performing different control for a case wherein vertical direction body motion is detected and a case wherein horizontal direction body motion is detected.

Also, the present invention can be applied to various types of music playback devices such as portable hard disk players, MD (MINIDISC (registered trademark)) players, portable information terminals or cellular telephone devices with music playback functions, and so forth, such that the vertical direction body motion of the user is accurately detected, the tempo of the vertical direction body motion of the user is comprehended from the cycle of vertical direction body motion, and the playback tempo of the music is controlled so as to match the tempo of the body motion of the user. Of course, control can be made corresponding not only to vertical direction body motion but also horizontal direction body motion.

Note that here, the playback tempo of music is the speed of playback of the music data, meaning the number of beats per minute (BPM: Beat Per Minutes). Also, the tempo of body motion of the user means the number of smallest measurable body motion units (one action (body motion)) per minute, which is bodily the speed of actions (body motions) which is the number of steps per minute in the case that the actions (body motions) of the user are walking or running or the like, and in the case that the action is jumping, is the number of jumps per minute, and so forth.

Thus, the present invention does not only accurately detect body motions of the user, but can also comprehend the tempo of body motions and perform playback control of contents such as music (songs) accordingly. Of course, this is not restricted to playback control of music and the like, and is applicable to cases of controlling the operations of various types of devices to be controlled corresponding to body motions of the user.

The invention claimed is:

1. A body motion detecting device comprising:
   a multi-axial acceleration sensor;
   acceleration-of-gravity calculating means for calculating an acceleration-of-gravity vector from acceleration vectors, which are detection outputs of said multi-axial acceleration sensor;
   vertical component extracting means for extracting a vertical component of acceleration, using said acceleration vectors from said acceleration sensor and said acceleration-of-gravity vector calculated by said acceleration-of-gravity calculating means;
   peak detection means for detecting peaks in said vertical component of acceleration extracted by said vertical component extracting means; and
   vertical body motion detecting means for detecting body motion in the vertical direction by analyzing said peaks detected by said peak detection means,
   wherein the acceleration-of-gravity calculating means recalculates the acceleration-of-gravity vector after the vertical component of acceleration is extracted, by the vertical component extracting means, from the acceleration-of-gravity vector a predetermined number of times.

2. The body motion detecting device according to claim 1, further comprising counting means for counting said body motion in the vertical direction detected by said vertical body motion detecting means.

3. A body motion detecting device comprising:
   a multi-axial acceleration sensor;
   acceleration-of-gravity calculating means for calculating an acceleration-of-gravity vector from acceleration vectors, which are detection outputs of said multi-axial acceleration sensor;
   horizontal component extracting means for extracting a horizontal component of acceleration, based on a computational expression corresponding to an angle of deviation in three-dimensional space of the acceleration vectors from said acceleration sensor and said acceleration-of-gravity vector calculated by said acceleration-of-gravity calculating means;
   peak detection means for detecting peaks in said horizontal component of acceleration extracted by said horizontal component extracting means; horizontal body motion detecting means for detecting body motion in the horizontal direction by analyzing said peaks detected by said peak detection means; and
   control means for forming control signals corresponding to said body motion in the horizontal direction detected by said horizontal body motion detecting means.

4. A body motion detecting method comprising:
   calculating an acceleration-of-gravity vector from acceleration vectors, which are detection outputs of a multi-axial acceleration sensor;
   extracting a vertical component of acceleration, using said acceleration vectors from said acceleration sensor and said acceleration-of-gravity vector calculated in said calculating;
   detecting peaks in said vertical component of acceleration extracted in said extracting; detecting body motion in the vertical direction by analyzing said peaks detected in said detecting peaks; and
   recalculating the acceleration-of-gravity vector after the vertical component of acceleration is extracted, by the extracting, from the acceleration-of-gravity vector a predetermined number of times.

5. The body motion detecting method according to claim 4, further comprising counting said body motion in the vertical direction detected in said detecting body motion.

6. A body motion detecting method comprising:
   calculating an acceleration-of-gravity vector from acceleration vectors, which are detection outputs of a multi-axial acceleration sensor;
   extracting a horizontal component of acceleration, based on a computational expression corresponding to an angle of deviation in three-dimensional space of the acceleration vectors from said acceleration sensor and said acceleration-of-gravity vector calculated in said calculating;

detecting peaks in said horizontal component of acceleration extracted in said extracting; detecting body motion in the horizontal direction by analyzing said peaks detected in said detecting peaks; and forming control signals corresponding to said body motion in the horizontal direction detected in said detecting body motion.

7. A non-transitory computer-readable storage medium storing computer executable instructions, which when executed by a computer, cause the computer to perform a method for detecting body motion of a user, the method comprising:

receiving supply of detection outputs from a multi-axial acceleration sensor;

calculating an acceleration-of-gravity vector from acceleration vectors, which are said detection outputs of said multi-axial acceleration sensor;

extracting a vertical component of acceleration, using said acceleration vectors from said acceleration sensor and said acceleration-of-gravity vector calculated in said calculating;

detecting peaks in said vertical component of acceleration extracted in said extracting; detecting body motion in the vertical direction by analyzing said peaks detected in said detecting peaks; and recalculating the acceleration-of-gravity vector after the vertical component of acceleration is extracted, by the extracting, from the acceleration-of-gravity vector a predetermined number of times.

8. The non-transitory computer-readable storage medium according to claim 7, wherein the method further comprises counting said body motion in the vertical direction detected in said detecting body motion.

9. A non-transitory computer-readable storage medium storing computer executable instructions, which when executed by a computer, cause the computer to perform a method for detecting body motion of a user, the method comprising:

receiving supply of detection outputs from a multi-axial acceleration sensor;

calculating an acceleration-of-gravity vector from acceleration vectors, which are said detection outputs of said multi-axial acceleration sensor;

extracting a horizontal component of acceleration, based on a computational expression corresponding to an angle of deviation in three-dimensional space of the acceleration vector from said acceleration sensor and said acceleration-of-gravity vector calculated in said calculating;

detecting peaks in said horizontal component of acceleration extracted in said extracting; detecting body motion in the horizontal direction by analyzing said peaks detected in said detecting peaks; and forming control signals corresponding to said body motion in the horizontal direction detected in said detecting body motion.

10. A body motion detecting device comprising:
a multi-axial acceleration sensor;
an acceleration-of-gravity calculating section configured to calculate an acceleration-of-gravity vector from acceleration vectors, which are detection outputs of said multi-axial acceleration sensor;

a vertical component extracting section configured to extract a vertical component of acceleration, using said acceleration vectors from said acceleration sensor and said acceleration-of-gravity vector calculated by said acceleration-of-gravity calculating section;

a peak detection section configured to detect peaks in said vertical component of acceleration extracted by said vertical component extracting section; and a vertical body motion detecting section configured to detect body motion in the vertical direction by analyzing said peaks detected by said peak detection section, wherein the acceleration-of-gravity calculating section is further configured to recalculate the acceleration-of-gravity vector after the vertical component of acceleration is extracted, by the vertical component extracting section, from the acceleration-of-gravity vector a predetermined number of times.

11. The body motion detecting device according to claim 10, further comprising a counting section configured to determine a number of steps as the body motion by counting the peaks detected by said peak detection section.

12. A body motion detecting device comprising:
a multi-axial acceleration sensor;
an acceleration-of-gravity calculating section configured to calculate an acceleration-of-gravity vector from acceleration vectors, which are detection outputs of said multi-axial acceleration sensor;

a horizontal component extracting section configured to extract a horizontal component of acceleration, based on a computational expression corresponding to an angle of deviation in three-dimensional space of the acceleration vectors from said acceleration sensor and said acceleration-of-gravity vector calculated by said acceleration-of-gravity calculating section;

a peak detection section configured to detect peaks in said horizontal component of acceleration extracted by said horizontal component extracting section;

a horizontal body motion detecting section configured to detect body motion in the horizontal direction by analyzing said peaks detected by said peak detection section; and a counting section configured to determine a number of horizontal shakes as the body motion by counting the peaks detected by said peak detection section.

13. The body motion detecting device according to claim 12, further comprising:
a control section configured to determine an on/off state of the body motion detecting device based on the number of horizontal shakes counted by the counting section.

14. The body motion detecting device according to claim 12, further comprising:
the acceleration-of-gravity calculating section further configured to recalculate the acceleration-of-gravity vector after the horizontal component of acceleration is extracted from the acceleration-of-gravity vector a predetermined number of times.

15. A body motion detecting device comprising:
a multi-axial acceleration sensor;
an acceleration-of-gravity calculating section configured to calculate an acceleration-of-gravity vector from acceleration vectors, which are detection outputs of said multi-axial acceleration sensor;

a horizontal component extracting section configured to extract a horizontal component of acceleration, based on a computational expression corresponding to an angle of deviation in three-dimensional space of the acceleration vectors from said acceleration sensor and said acceleration-of-gravity vector calculated by said acceleration-of-gravity calculating section;
a peak detection section configured to detect peaks in said horizontal component of acceleration extracted by said horizontal component extracting section;
a horizontal body motion detecting section configured to detect body motion in the horizontal direction by analyzing said peaks detected by said peak detection section; and
a control section configured to form control signals corresponding to said body motion in the horizontal direction detected by said horizontal body motion detecting means.

16. A body motion detecting device comprising:
a multi-axial acceleration sensor;
acceleration-of-gravity calculating means for calculating an acceleration-of-gravity vector from acceleration vectors, which are detection outputs of said multi-axial acceleration sensor;
horizontal component extracting means for extracting a horizontal component of acceleration, based on a computational expression corresponding to an angle of deviation in three-dimensional space of the acceleration vectors from said acceleration sensor and said acceleration-of-gravity vector calculated by said acceleration-of-gravity calculating means;
peak detection means for detecting peaks in said horizontal component of acceleration extracted by said horizontal component extracting means;
horizontal body motion detecting means for detecting body motion in the horizontal direction by analyzing said peaks detected by said peak detection means; and
counting means for determining a number of horizontal shakes as the body motion by counting the peaks detected by said peak detection means.

17. A body motion detecting method comprising:
calculating an acceleration-of-gravity vector from acceleration vectors, which are detection outputs of a multi-axial acceleration sensor;
extracting a horizontal component of acceleration, based on a computational expression corresponding to an angle of deviation in three-dimensional space of the acceleration vectors from said acceleration sensor and said acceleration-of-gravity vector calculated in said calculating;
detecting peaks in said horizontal component of acceleration extracted in said extracting;
detecting body motion in the horizontal direction by analyzing said peaks detected in said detecting peaks; and
determining a number of horizontal shakes as the body motion by counting the peaks detected by said detecting peaks.

18. A non-transitory computer-readable storage medium storing computer executable instructions, which when executed by a computer, cause the computer to perform a method for detecting body motion of a user, the method comprising:
receiving supply of detection outputs from a multi-axial acceleration sensor;
calculating an acceleration-of-gravity vector from acceleration vectors, which are said detection outputs of said multi-axial acceleration sensor;
extracting a horizontal component of acceleration, based on a computational expression corresponding to an angle of deviation in three-dimensional space of the acceleration vector from said acceleration sensor and said acceleration-of-gravity vector calculated in said calculating;
detecting peaks in said horizontal component of acceleration extracted in said extracting;
detecting body motion in the horizontal direction by analyzing said peaks detected in said detecting peaks; and
determining a number of horizontal shakes as the body motion by counting the peaks detected by said detecting peaks.

19. A body motion detecting device comprising:
a multi-axial acceleration sensor;
acceleration-of-gravity calculating means for calculating an acceleration-of-gravity vector from acceleration vectors, which are detection outputs of said multi-axial acceleration sensor;
horizontal component extracting means for extracting a horizontal component of acceleration, based on a computational expression corresponding to an angle of deviation in three-dimensional space of the acceleration vectors from said acceleration sensor and said acceleration-of-gravity vector calculated by said acceleration-of-gravity calculating means;
peak detection means for detecting peaks in said horizontal component of acceleration extracted by said horizontal component extracting means; and
horizontal body motion detecting means for detecting body motion in the horizontal direction by analyzing said peaks detected by said peak detection means,
wherein the acceleration-of-gravity calculating means recalculates the acceleration-of-gravity vector after the horizontal component of acceleration is extracted, by the horizontal component extracting means, from the acceleration-of-gravity vector a predetermined number of times.

20. A body motion detecting method comprising:
calculating an acceleration-of-gravity vector from acceleration vectors, which are detection outputs of a multi-axial acceleration sensor;
extracting a horizontal component of acceleration, based on a computational expression corresponding to an angle of deviation in three-dimensional space of the acceleration vectors from said acceleration sensor and said acceleration-of-gravity vector calculated in said calculating;
detecting peaks in said horizontal component of acceleration extracted in said extracting;
detecting body motion in the horizontal direction by analyzing said peaks detected in said detecting peaks; and
recalculating the acceleration-of-gravity vector after the horizontal component of acceleration is extracted, by the extracting, from the acceleration-of-gravity vector a predetermined number of times.

21. A non-transitory computer-readable storage medium storing computer executable instructions, which when executed by a computer, cause the computer to perform a method for detecting body motion of a user, the method comprising:
receiving supply of detection outputs from a multi-axial acceleration sensor;
calculating an acceleration-of-gravity vector from acceleration vectors, which are said detection outputs of said multi-axial acceleration sensor;
extracting a horizontal component of acceleration, based on a computational expression corresponding to an angle of deviation in three-dimensional space of the acceleration vector from said acceleration sensor and said acceleration-of-gravity vector calculated in said calculating;

detecting peaks in said horizontal component of acceleration extracted in said extracting;

detecting body motion in the horizontal direction by analyzing said peaks detected in said detecting peaks; and recalculating the acceleration-of-gravity vector after the horizontal component of acceleration is extracted, by the extracting, from the acceleration-of-gravity vector a predetermined number of times.

22. A body motion detecting device comprising:

a multi-axial acceleration sensor;

an acceleration-of-gravity calculating section configured to calculate an acceleration-of-gravity vector from acceleration vectors, which are detection outputs of said multi-axial acceleration sensor;

a horizontal component extracting section configured to extract a horizontal component of acceleration, based on a computational expression corresponding to an angle of deviation in three-dimensional space of the acceleration vectors from said acceleration sensor and said acceleration-of-gravity vector calculated by said acceleration-of-gravity calculating section;

a peak detection section configured to detect peaks in said horizontal component of acceleration extracted by said horizontal component extracting section;

a horizontal body motion detecting section configured to detect body motion in the horizontal direction by analyzing said peaks detected by said peak detection section, wherein the acceleration-of-gravity calculating section is further configured to recalculate the acceleration-of-gravity vector after the horizontal component of acceleration is extracted, by the extracting, from the acceleration-of-gravity vector a predetermined number of times.

* * * * *